(12) United States Patent
Antwi

(10) Patent No.: US 9,744,115 B2
(45) Date of Patent: Aug. 29, 2017

(54) NATURAL PERSONAL CARE CREAM TO POWDER COMPOSITIONS

(71) Applicant: The Burt's Bees Products Company, Oakland, CA (US)

(72) Inventor: Abena Antwi, Durham, NC (US)

(73) Assignee: The Clorox Company, Oakland, CA (US)

(*) Notice: Subject to any disclaimer, the term of this patent is extended or adjusted under 35 U.S.C. 154(b) by 0 days.

(21) Appl. No.: 14/172,606

(22) Filed: Feb. 4, 2014

(65) Prior Publication Data

US 2015/0216785 A1 Aug. 6, 2015

(51) Int. Cl.
| | | |
|---|---|---|
| *A61K 8/73* | (2006.01) | |
| *A61K 8/34* | (2006.01) | |
| *A61K 8/37* | (2006.01) | |
| *A61K 8/60* | (2006.01) | |
| *A61Q 19/00* | (2006.01) | |

(52) U.S. Cl.
CPC ............. *A61K 8/732* (2013.01); *A61K 8/342* (2013.01); *A61K 8/37* (2013.01); *A61K 8/375* (2013.01); *A61K 8/60* (2013.01); *A61K 8/602* (2013.01); *A61Q 19/00* (2013.01); *A61K 2800/30* (2013.01)

(58) Field of Classification Search
CPC .......... A61K 8/732; A61K 8/342; A61K 8/37; A61K 8/375; A61K 8/60; A61K 8/602; A61Q 19/00
See application file for complete search history.

(56) References Cited

U.S. PATENT DOCUMENTS

| | | | |
|---|---|---|---|
| 4,568,539 A | 2/1986 | Ashton et al. | |
| 4,913,896 A | 4/1990 | Harvey | |
| 5,338,535 A | 8/1994 | Berndt | |
| 6,267,970 B1 | 7/2001 | Matesevac et al. | |
| 6,458,372 B1 | 10/2002 | Scordamaglia-Crockett et al. | |
| 7,455,849 B2 | 11/2008 | Utschig et al. | |
| 7,547,443 B2 | 6/2009 | Krzysik et al. | |
| 8,283,299 B2 | 10/2012 | Allef et al. | |
| 2006/0057217 A1* | 3/2006 | Utschig ................. | A61K 8/732 424/489 |
| 2007/0098661 A1 | 5/2007 | Maxon | |
| 2008/0145443 A1 | 6/2008 | Langolf et al. | |
| 2010/0055061 A1 | 3/2010 | Mandelli et al. | |
| 2012/0328544 A1* | 12/2012 | Stockel .................. | A61K 8/361 424/61 |
| 2014/0086852 A1* | 3/2014 | Pham ...................... | A61Q 5/12 424/59 |

OTHER PUBLICATIONS

Mellowship, D. (2012) What chemical ingredients are in beauty products? [online] [Retrieved on Feb. 26, 2016] Retrieved from <http://www.natureandhealth.com.au/news/what-chemical-ingredients-are-in-beauty-products>.*
Benefits of Using Natural & Organic Skincare Products. (2013) [online] Retrieved on Feb. 27, 2016] Retrieved from <http://www.abesmarket.com/blog/favorite-products/go-behind-beauty-with-abes-experts/.*
Jha, B., Meyer, J., Polak, G. (2010) Integrating Natural, Sustainable and Performance Characteristics in Personal Care Products. SOFW-Journal, v. 136, p. 36, 38, 40, 42, 44 and 45.*
Hydrior: Polyglycerol Esters for successful cosmetics formulations. (2008) [online] [Retrieved on Feb. 24, 2016] Retrieved from <http://www.in-cosmetics.com/_novadocuments/37619?v=635260873579430000>.*
Emolid CC—Natural Spreadability (2013) [online] [Retrieved on Feb. 24, 2016] Retrieved from <www.iqlasem.com/media_items/file/QL_Emolid%20CC-2013.pdf>.*
Dermofeel® MCT (2005) [online] [Retrieved on Feb. 29, 2016] Retrieved from <http://www.dr-straetmans.de/en/products/productdescription_dermofeel_mct.php>.*

* cited by examiner

Primary Examiner — Jonathan S Lau
(74) Attorney, Agent, or Firm — Ann Lee

(57) ABSTRACT

Personal care compositions that apply as a cream and quickly dry to a powdery feel. The compositions comprise a natural starch component (e.g., corn starch), water, one or more emulsifiers, and one or more emollients. The starch, emulsifiers, and emollients are naturally derived, naturally processed, or both. The composition advantageously does not require the addition of synthetic gelling agents or other suspension aids to maintain the starch component in suspension, even with relatively low water concentrations and relatively high starch concentrations. In an embodiment, the emollients include esters of fatty acids and fatty alcohols, as well as a tertiary branched ester (a triester). The emulsifiers may include a sugar ester, alkylaryl glucoside, alkyl aryl alcohol, and straight chain fatty alcohol. An ester of a polyglycerin and a fatty acid (e.g., polyglyceryl-4 caprate) stabilizer has surprisingly been found to provide high temperature phase stability to the composition.

14 Claims, No Drawings

NATURAL PERSONAL CARE CREAM TO POWDER COMPOSITIONS

BACKGROUND OF THE INVENTION

1. The Field of the Invention

The present invention relates generally to cream to powder compositions that are applied topically as a cream and dry to a powder or powder-like consistency or feel on skin. The composition may be produced from a limited number of naturally-derived, naturally-processed, GRAS (generally recognized as safe), biodegradable ingredients, and have good spreadability (like a cream), while providing a soft powdery feel (like a powder).

2. Description of Related Art

Personal care compositions have progressed and created a large chemical industry devoted to developing new synthetic emulsifiers, suspending agents, viscosity-controlling agents, etc. to achieve ever improving solids-containing products for the consumer. There are currently over ten thousand different synthetic chemicals used in personal care products intended for use on human skin. Although these synthetic chemicals have been tested on animals at some stage, they have never been tested for long term health affects either individually or in combination. Even the majority of those that actually have been found to cause an adverse health effect to some members of the population can still be used.

Personal care solids-containing formulations typically include multiple synthetic ingredients, many of which have suspected human health risks as indicated by peer-reviewed third-party scientific literature. For example, hydroxyethyl acrylate/sodium acrylate acryloyldimethyl taurate copolymer, aluminum starch octenylsuccinate, methylisothiazolinone, PEG-20 methyl glucose seqsquistearate, and capryl glycol are examples of ethoxylated synthetic ingredients commonly found in personal care solids-containing formulations. In addition, parabens; glycols; phthalates; and other ethoxylated ingredients such as sodium myreth sulfate, sodium laureth sulfate, PEGs (polyethylene glycol) and PPGs (polypropylene glycol); ethanolamines such as DEAs (diethanolamine), MEAs (monoethanolamine), TEAs (triethanolamine); synthetic polymers such as PVP (polyvinylpyrrolidone) and acrylates; and formaldehyde donors such as DMDM hydantoin, diazolidinyl urea and methylisothiazolinone are often employed. Significant fractions of volatile components (e.g., more volatile than water) are also often employed in such compositions to achieve desired characteristics.

In addition to numerous synthetic ingredients, many personal care formulations may have otherwise natural ingredients that are synthetically-derived or processed. Processes such as ethoxylation, sulfination or polymerization have the potential to change the chemical make-up of ingredients that start out natural, but may not properly be characterized as such after processing. These types of processes dilute or change the composition of an ingredient, can involve caustic solvents, impurities and can leave residual compounds behind. Natural, ecological processes such as distillation, condensation, extraction, steam distillation, pressure cooking and hydrolysis are desirable where it is desired to maximize the purity of natural ingredients.

Because of a desire to use renewable resources and to eliminate contact with potentially harmful synthetic materials, natural-based personal care compositions are gaining increasing interest. Most of these personal care compositions contain only some natural ingredients with the majority of their components being synthetic. One difficulty in formulating all-natural (or nearly all-natural) personal care compositions is achieving acceptable consumer performance with a limited number of raw materials. The number of all-natural ingredients available is scarce when compared to the number of highly developed synthetic emulsifiers, synthetic moisturizers, emollients, and other synthetic ingredients.

For example, existing personal care solids-containing compositions that include only naturally-derived, naturally-processed, GRAS, biodegradable ingredients are not able to effectively suspend a solid powder such as corn starch in a formulation that can be applied to skin as a cream, which shortly thereafter dries to a powdery-like feel. For example, existing compositions typically include some natural ingredients (such as corn starch), but then include synthetic ethoxylated suspending agents (e.g., acrylate copolymers) to keep such solids from settling. Existing personal care solids-containing compositions do not have at least 95% of the components of the product originating from renewable sources found in nature. Moreover, existing personal care solids-containing compositions do not have at least 95% of the components derived from natural, ecological processes. Embodiments of the present invention provide a personal care solids-containing composition that overcomes the disadvantages and shortcomings associated with those of the prior art.

BRIEF SUMMARY OF THE INVENTION

According to one embodiment, the present invention relates to compositions that are applied as a cream, but which quickly dry to a powdery-like feel. Such compositions may be employed for use as a baby powder composition, e.g., in prevention of diaper rash in infants. Such compositions may be employed in other uses where it is desired to apply a composition as an easily spreadable cream, which immediately thereafter dries to a solid powdery feel, e.g., other treatment creams such as make up (e.g., a foundation), other cosmetics, etc.

According to an embodiment, the present compositions achieve suspension of a solid starch component (e.g., corn starch), with only a limited amount of water in the composition, and while only using emulsifiers, emollients, stabilizers, and other components to achieve suspension or other features where these components are all naturally-derived, naturally-processed, or both. In one embodiment, the suspension system consists of or consists essentially of components that are naturally-derived, naturally-processed, or both. In one embodiment, not only is the suspension system naturally-based, but nearly the entire (or the entire) personal care composition includes only naturally-derived, naturally-processed components (e.g., 95% or more, 97% or more, or 99% or more natural-based components). Such compositions may be free of or substantially free of components made using ethoxylating processes, such as acrylate copolymers, ethoxy succinates, isothiazolinones, glycols, ethanolamines, sulfates, etc.

Such ethoxylated components are ubiquitously used in various personal care products to keep solids (e.g., corn starch) from settling, to thicken the composition, and for other purposes. While various synthetic ethoxylated components exhibit excellent ability to suspend solids and to thicken cream or lotion compositions, these synthetic materials are not naturally-derived or naturally-processed, and there are suspected health risks associated with their use. As such, a need exists for suspension systems, thickener systems, etc. that include only components that are naturally-derived and/or naturally processed.

The present inventor has surprisingly found that even very high starch concentrations (e.g., where starch is the major component, present at a higher concentration than any other component), and at relatively low water concentrations (e.g., less water than starch), it is possible to achieve a stable suspension of the solid starch component using only natural-derived and/or naturally processed components. Furthermore, the composition may exhibit phase stability (i.e., resistance to solid-component settling or other phase separation), spreadability, and other aesthetic characteristics such as feel upon application that are similar to those provided by compositions including synthetic components.

According to an embodiment, the composition comprises water, one or more natural starch components, one or more emulsifiers, and one or more emollients. The water comprises no more than about 35% of the composition by weight, while the natural starch components comprise at least about 35% of the composition by weight (e.g., the composition may typically comprise more starch than water). The starch components, emulsifiers, and emollients of the composition may advantageously be naturally derived, naturally processed, or both.

According to another embodiment, the composition comprises water, one or more natural starch components, an emulsifier and thickener blend, an emollient blend, and one or more stabilizers. The emulsifier and thickener blend comprises a sugar ester and wax, the emollient blend includes emollients of different polarity characteristics, and the stabilizer comprises an ester of a fatty acid and polyglycerin. The water is included in a concentration that is lower than the concentration of starch. The water comprises no more than 35% of the composition by weight, while the starch comprises at least 35% of the composition by weight. The starch components, emulsifiers, emollients, and stabilizers of the composition may advantageously be naturally derived, naturally processed, or both.

According to another embodiment, the composition comprises water, one or more natural starch components, an emulsifier and thickener blend, an emollient blend, and one or more stabilizers. The emulsifier and thickener blend comprises a sugar ester, wax, an alkylaryl glucoside, an alkylaryl alcohol, and a straight chain fatty alcohol. The emollient blend includes different esters of fatty alcohols and fatty acids, the esters having different polarity characteristics. The stabilizer comprises an ester of a fatty acid and polyglycerin (e.g., polygylceryl-4 caprate). The water is included in a concentration that is lower than the concentration of starch. The water comprises no more than 35% of the composition by weight, while the starch comprises at least 35% of the composition by weight. The starch components, emulsifiers, emollients, and stabilizers of the composition may advantageously be naturally derived, naturally processed, or both.

The features and advantages of compositions of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE PREFERRED EMBODIMENTS

I. Definitions

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

References herein to "one embodiment", "one aspect" or "one version" of the invention include one or more such embodiment, aspect or version, unless the context clearly dictates otherwise.

As used in this specification and the appended claims, the singular forms "a", "an", and "the" include plural referents unless the context clearly dictates otherwise.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("%'s") are in weight percent (based on 100% active) of the active composition alone, unless otherwise indicated.

Disclosed herein are preferred ranges. It is to be understood that values representing upper or lower ceiling values (e.g., at least 10%) or values representing ranges (e.g., from 10% to 20%) are inclusive of all values therebetween, (e.g., at least 10% is inclusive of at least 8.5% and from 10% to 20% is inclusive of from 12.2% to 17%, etc.).

The term "comprising", which is synonymous with "including," "containing," or "characterized by," is inclusive or open-ended and does not exclude additional, unrecited elements or method steps. See MPEP 2111.03. See, e.g., Mars Inc. v. H.J. Heinz Co., 377 F.3d 1369, 1376, 71 USPQ2d 1837, 1843 (Fed. Cir. 2004) ("like the term 'comprising,' the terms 'containing' and 'mixture' are open-ended."). Invitrogen Corp. v. Biocrest Mfg., L.P., 327 F.3d 1364, 1368, 66 USPQ2d 1631, 1634 (Fed. Cir. 2003) ("The transition 'comprising' in a method claim indicates that the claim is open-ended and allows for additional steps."); Genentech, Inc. v. Chiron Corp., 112 F.3d 495, 501, 42 USPQ2d 1608, 1613 (Fed. Cir. 1997) See MPEP 2111.03. ("Comprising" is a term of art used in claim language which means that the named elements are essential, but other elements may be added and still form a construct within the scope of the claim.); Moleculon Research Corp. v. CBS, Inc., 793 F.2d 1261, 229 USPQ 805 (Fed. Cir. 1986); In re Baxter, 656 F.2d 679, 686, 210 USPQ 795, 803 (CCPA 1981); Ex parte Davis, 80 USPQ 448, 450 (Bd. App. 1948). See MPEP 2111.03.

The term "consisting essentially of" as used herein, limits the scope of a claim to the specified materials or steps "and those that do not materially affect the basic and novel characteristic(s)" of the claimed invention. In re Herz, 537 F.2d 549, 551-52, 190 USPQ 461, 463 (CCPA 1976) (emphasis in original). See MPEP 2111.03.

The term "consisting of" as used herein, limits the scope of a claim to the specified materials or steps, indicating that the claim or limitation to which it pertains is closed, not allowing for additional steps or materials.

The term "naturally-derived" as used herein is meant to mean that the ingredient comes or is made from a renewable resource found in nature (i.e., Flora, Fauna, Mineral). Petroleum compounds are expressly excluded from the term "naturally-derived".

The term "naturally-processed" as used herein means the ingredients are processed using only ecologically-friendly processes. Ecologically-friendly processing is minimal processing that maximizes purity and minimizes negative effects on the ingredients. Only biodegradable reagents are used in ecologically-friendly processing. Naturally-processed as used herein includes, but is not limited to, distillation, condensation, extraction, steamed distillation, pressure cooking and hydrolysis.

Other examples of natural processes include: saponification which uses a strong alkali base (e.g., NaOH) to create a reaction with a fat or oil to produce soap, glycerin and water in one process; esterification and transesterification which involve reacting an alcohol and an acid or base to create safe emulsifiers, stabilizers and solubilizers that thicken, hydrate, and/or moisturize; and biofermentation which converts substances through the use of a yeast and/or a bacteria to produce nutrients and/or to purify formulations. The microorganisms typically do not survive the process.

When a component is described as being naturally-derived and naturally-processed, it is meant that the component is naturally-derived, and if any processing is performed, the processing is natural. Some naturally-derived components may not require any processing, and such components still qualify as naturally-derived and naturally processed.

Several processes dilute or change the composition of an ingredient to the point that an otherwise natural ingredient becomes "unnatural" by virtue of how it is processed. Ethoxylation, sulfonation and polymerization processes are expressly excluded from the term "naturally-processed". For example, sulfonation uses harsh processing that involves sulfates, sulfonates and/or phosphates to create effective wetting agents for use in detergents and foaming agents. Such processes are excluded from the definition of "naturally-processed" because sulfates do not break down in the environment. Ethoxylation also uses harsh processing. A byproduct of ethoxylation is 1,4 dioxane, which is carcinogenic. In addition, such materials often degrade to form products that are toxic to aquatic life (e.g., degradation of ethoxylates to nonylphenol). One example of a common naturally-derived synthetic substitute produced by processes such as sulfonation and ethoxylation is sodium lauryl/laureth sulfate (SLS). SLS is derived from coconut oil, but is processed in such a way that does not render it an "eco-friendly, natural" ingredient as the term is used herein.

The term "GRAS" as used herein is meant to mean generally recognized as safe (GRAS) by the Food and Drug Administration (FDA) when used in accordance with the FDA's good manufacturing practices (GMP) and contain no residues of heavy metals or other contaminants in excess of tolerances set by the FDA or the EPA.

The term "biodegradable" as used herein refers to carbon containing materials that can be degraded by microbial action. The "biodegradable" materials may be tested under a recognized protocol and with tested methods of established regulatory bodies such as: EPA, EPA- TSCA, OECD, MITI or other similar or equivalent organizations in the US or internationally. Suitable non-limiting examples of test methods for biodegradation include: OECD methods in the 301-305 series. Generally, all "biodegradable" materials must meet the following limitations: (a) removal of dissolved organic carbon >70%, (b) biological oxygen demand (BOD) >60%, (c) % of BOD of theoretical oxygen demand >60%, and (d) % $CO_2$ evolution of theoretical >60%.

The term "eco-friendly, natural ingredient" and similar descriptors refers to an ingredient that is naturally-derived, naturally-processed, GRAS and biodegradable.

In one embodiment, the personal care compositions of the present invention contain at least 95% naturally-derived, naturally-processed, GRAS, biodegradable ingredients. Unlike prior art formulations which include a subset of the components which may be "natural" ingredients, but which also include significant fractions of synthetic, non eco-friendly components for purposes of emulsification, thickening, etc., the compositions of the present invention include no or essentially no synthetic, non eco-friendly components, while exhibiting emulsification, thickening, and stability characteristics that are as good or better than those including synthetic or quasi-synthetic components.

II. Introduction

One embodiment of the present invention is directed to personal care compositions that apply as a cream and quickly dry to a powdery feel. The composition may advantageously not include any components that are not eco-friendly (e.g., ethoxylates, etc.), while still achieving a stable emulsified composition. Such a composition may include water, one or more natural starch components (e.g., corn starch), one or more emulsifiers, and one or more emollients, where the water, starch, emulsifiers, and emollients are all naturally-derived, naturally processed, or both. The water may comprise no more than about 35% by weight of the composition, while the starch component may comprise at least about 35% by weight of the composition. The inventor has found that it is very difficult to achieve thickening and a stable emulsion without phase separation, particularly at elevated storage temperatures, with such compositions that include a relatively large fraction of starch to water (e.g., including more starch than water), without the use of conventional synthetic non eco-friendly suspension aids, thickeners, and emulsifiers. However, embodiments of compositions of the present invention may be free of or substantially free of synthetic components including, but not limited to, synthetic ethoxylates, acrylate polymers, acrylate copolymers, isothiazolinones, methicones, esterified or other modified starch derivatives or salts thereof (e.g., aluminum starch octenylsuccinate), polyethylene oxides, polyethylene glycols. Such embodiments may also be free of volatile components (i.e., components having greater volatility than that of water, e.g., lower alcohols such as ethanol).

Such personal care compositions may include diaper cream and baby powder compositions applied to a baby's diaper area to prevent diaper rash (e.g., by acting as a barrier to wetness). Other uses and similar compositions where a powder component (e.g., capable of hydration) is emulsified into a small amount of water, while using only naturally-derived, naturally-processed emulsifiers, thickeners, emollients, etc. may also be within the scope of the present invention where it is desired to apply a composition as a cream, which composition dries to a powdery feel immediately after being rubbed into the skin (e.g., make-up foundation).

III. Exemplary Personal Care Compositions

A. Starch Component

The cream to powder compositions according to the present invention include one or more natural starch components. Such starches are generally polysaccharides of natural origin. Such starches generally include a large number of glucose units joined together by glycosidic bonds. Such starches may be extracted or derived from various natural plant sources (e.g., vegetable starches) such as from corn, wheat, rice, other grains, potatoes, etc. Corn starch (*zea mays*) is an example of a particularly preferred starch suitable for use in embodiments of the cream to powder compositions of the present invention.

Starch typically includes two types of molecules, the linear amylose and the branched amylopectin. The ratio of amylose to amylopectin depends on the source of the starch. Often, the amylose content may range from about 20% to 25% by weight, while the amylopectin may be 75% to 80% by weight. Higher and lower amylose and amylopectin fractions are available depending on the starch source.

The starch may be the most prevalent component included within the composition, included in an amount greater than any other component, including the amount of added water. For example, the starch may be present within the composition in a range of at least 35%, at least 40%, from about 35% to about 50%, and from about 35% to about 45%. The starch component used in manufacture of the composition may itself include a moisture content of water that is bound to the starch. For example, a moisture content of the starch may be less than about 15% of the starch by weight (e.g., about 10% to about 13%). Lower moisture contents may of course also be suitable for use (e.g., less than 10%, less than 5%, etc.).

B. Water

The cream to powder compositions according to the present invention include water. The amount of added water (i.e., not including any moisture content already present within the starch or other components) may be less than about 35% by weight of the composition, or less than 30% by weight of the composition. In an embodiment, the concentration of added water may be less than the concentration of the starch component.

In an embodiment, the composition may advantageously be formulated as a cream, rather than a lotion. The difference between a cream versus a lotion may be related to water content of the composition. For example, a lotion may have a water content of at least about 70% or more of the composition, while a cream may be substantially lower. For example, a cream may have a water content lower than 50%, lower than 40%, or even lower. For example, the present cream to powder compositions which upon dispensing from a container exhibit cream consistency characteristics, may have a very low water content, of less than 35%, or less than 30%. As described above, the water content may be less than that of the starch component, such that the composition is a very low water content cream.

The low water content facilitates quick evaporation of the water from the composition, or its incorporation into the starch component (e.g., hydration of the starch), providing a composition that immediately upon rubbing the composition into the skin, assumes a powdery feel (i.e., upon rubbing into the skin, the composition feels like a powder).

The composition may advantageously be free or substantially free of volatile components having a volatility greater than that of the water component. For example, the composition may be void of lower alcohols (e.g., $C_1$-$C_4$ alcohols) such as ethanol, propanol, isopropanol, etc.

The compositions may be thickened through the starch and water component, as well as with the emulsifier blend, emollient blend, and wax (e.g., beeswax). The composition may be free of any synthetic gelling agent or thickening agent specifically added for this purpose (e.g., such as polyacrylate cross-polymer, methyl methacrylates, acrylate/$C_{10}$-$C_{30}$ alkylacrylate, and other acrylates or methacrylates). The composition may be semi-solid, rather than a thin, relatively low viscosity liquid or of a lotion consistency (i.e., relatively high water content with low viscosity). Specific rheological measurements of the formulation are difficult due to wall slip of the sample at the test apparatus spindle surface, entrapment of air in the sample, etc. Nevertheless, the semi-solid cream may have a consistency that is sufficiently thick so as to hold its shape (e.g., hold peaks, etc. similar to beaten egg whites) for a period of at least 1 minute, at least 3 minutes, at least 10 minutes, at least 1 hour, at least 1 day, etc.). The composition may harden in substantially the same shape as dispensed, if allowed to dry (e.g., if it were allowed to dry rather than being immediately rubbed into the skin.

In an embodiment, the composition may be void or substantially void of polyols that are not naturally-derived and/or naturally-processed. Such components are often included as carrier components in conventional formulations, and include, but are not limited to, polyethylene glycol, propylene glycol, and combinations thereof. At the same time, a polyol such as glycerin derived from natural sources, such as vegetable oil, may be included. Naturally-derived glycerin is an example of an eco-friendly polyol emollient carrier exhibiting humectant and moisturizing properties. Glycerin is a neutral, thick liquid which freezes to a gummy paste and which has a high boiling point. Glycerin can be dissolved into water or alcohol, but generally not into oils. In addition, many components can be dissolved into glycerin more easily than into water or alcohol. Thus, glycerin can be used to solubilize other components, including natural gums. Where naturally-derived glycerin is included, it may comprise no more than about 20%, no more than about 10%, no more than about 5%, no more than about 3%, no more than about 2%, or no more than about 1.5% of the composition.

C. Emulsifiers

An emulsifier is a substance which stabilizes an emulsion. While the corn starch may not technically be soluble, such that the starch component is a solid phase, and thus the term colloid rather than emulsion may be more technically accurate, the term emulsion may be used herein for sake of simplicity. As such, emulsifiers or suspension aids are frequently used in personal care products to stabilize the two phase composition, whether both phases are liquids or one is a liquid and another is a solid suspended therein. Examples of commonly used synthetic emulsifiers are fatty esters, silicones, polymers, and ethoxylates. Emulsifiers typically have a hydrophobic and a hydrophilic end. In oil-in-water emulsions, the emulsifiers will surround an oil (or other immiscible molecule) and form a protective layer so that the oil molecules cannot "clump" together. A similar mechanism may be responsible for suspension of a solid phase, preventing the solids from "clumping" together and precipitating. This action helps keep the dispersed phase in small droplets or particles and preserves the emulsion. The compositions of the present invention may include dispersed oil phases in addition to suspension and dispersion of the solid starch phase.

The present compositions are advantageously capable of achieving stable suspension of the solid starch component, even with the very low water concentrations as described above, without including any synthetic non eco-friendly emulsifiers or suspension aids. The emulsifier blend may include a sugar ester, an alkylaryl glucoside, an alkylaryl alcohol, and a fatty alcohol. For example, sucragel is a naturally-processed, naturally-derived oil thickening and emulsifying agent that is based on an ester of sucrose (e.g., sucrose laurate). Sucrose laurate is one example of a sugar ester. Other sugar esters may be based on disaccharides other than sucrose, such as, but not limited to, lactose, maltose, and combinations thereof. Esters of monosaccharides may also be suitable for use. Examples of monosaccharides include glucose, fructose, galactose, and combinations thereof. The disaccharide sucrose includes a glucose unit and a fructose unit. Various trisaccharides may also be suitable for use.

While sucrose laurate is an example of a suitable sugar ester, the laurate may be replaced with another hydrocarbon (e.g., an alkyl) chain including from 4 to 30 carbon atoms, from 6 to 20 carbon atoms, or from 12 to 18 carbon atoms. Various suitable fatty acid chains may be straight, branched, saturated, or unsaturated. In some embodiments, the hydrocarbon may be cyclic or aromatic.

Sucragel also includes glycerin and an alkyl triglyceride (e.g., caprylic and/or capric triglyceride). The alkyl chain of the alkyl triglyeride may have similar number of carbon atoms as described, above, e.g., from 4 to 30 carbon atoms, from 6 to 20 carbon atoms, or from 8 to 12 carbon atoms. For example, capric refers to a $C_8$ alkyl group, while caprylic refers to a $C_{10}$ alkyl group. Various suitable fatty acid chains may be straight, branched, saturated, or unsaturated. In some embodiments, the hydrocarbon may be cyclic or aromatic.

The glycerin included within the sucragel blend provides moisturizing benefits to the composition, while the capric/caprylic triglyceride is an effective emollient. The sucragel, including the sugar ester, is believed to be at least partially responsible for the excellent high temperature stability (i.e., lack of visible phase separation/precipitation of the solid components) exhibited by the present compositions.

The composition exhibits a homogenous creamy (e.g., white) appearance upon dispensing from the tube or other container, which coloration quickly dissipates upon rubbing the composition into the skin. The composition dries to a finish that is substantially colorless on the skin, without leaving any noticeable white or other colored casting residue. The composition exhibits a feel that is powdery and silky upon rubbing the composition into the skin, similar to the feel of a powdered composition that is dusted and then rubbed into the skin. As such, the composition provides a feel similar to that of a powdered dusting composition (e.g., a baby powder dispensed as a powder), but which is applied as a cream.

Application as a cream allows for much improved accuracy in placing the composition where desired, as the cream can be dispensed (as opposed to shaken or puffed, which generates a dust cloud) cleanly and with excellent accuracy and precision to only the location desired. Once a dab of the thick cream composition is applied, it can be rubbed into the skin. During rubbing, the color-cast (initially white) of the composition disappears, while the water may largely evaporate or be absorbed, leaving a powdery, silky sensation when rubbing in is completed. Once rubbed into the skin, no color-cast is readily apparent (although the composition will show up as white if the skin is then brushed against a black or other dark colored fabric).

The sucragel blend of components may comprise about 0.5% to about 10% of the composition by weight, from about 1% to about 5% of the composition by weight, or from about 2% to about 4% of the composition by weight. The sugar ester component of the sucragel may comprise about 0.01% to about 2% of the composition by weight, from about 0.05% to about 1% of the composition by weight, or from about 0.1% to about 0.5% of the composition by weight. The alkyl (e.g., capric/caprylic) triglyceride component and the glycerin of the sucragel may each comprise about 0.1% to about 5% of the composition by weight, from about 0.5% to about 2% of the composition by weight, or from about 1% to about 1.5% of the composition by weight. For example, the blend may include approximately equal fractions of the alkyl (e.g., capric/caprylic) triglyceride component and the glycerin.

In addition to the sucragel blend including the sugar ester, glycerin, and caprylic/capric triglyceride, the emulsifier blend may also include an alkylaryl glucoside, an alkylaryl alcohol, and/or a fatty alcohol, which all serve as emulsifiers. The alkyl chain of the alkylaryl glucoside may have from 4 to 30 carbon atoms, from 6 to 20 carbon atoms, or from 12 to 18 carbon atoms. Similarly, the alkyl chain of the alkylaryl alcohol may have from 4 to 30 carbon atoms, from 6 to 20 carbon atoms, or from 12 to 18 carbon atoms. Finally, the fatty alcohol may also have from 4 to 30 carbon atoms, from 6 to 20 carbon atoms, or from 12 to 18 carbon atoms. In an embodiment, each of the alkyl groups may have the same carbon chain length (e.g., all $C_{16}$-cetyl). For example, the emulsifier blend may include cetearyl glucoside, cetearyl alcohol, and cetyl alcohol. Such components may be derived from vegetable matter free of genetically modified organisms ("gmo-free"). The glucose may be extracted from, e.g., manioc, while the fat may be extracted from coconut oil. The cetearyl glucoside may thus be a glucolipid emulsifier in harmony with nature, and is capable of providing rich, smooth textures with any oil phase components.

The alkylaryl glucoside may comprise from about 0.1% to about 3% of the composition by weight, from about 0.25% to about 1% of the composition by weight, or from about 0.4% to about 0.8% of the composition by weight. The alkylaryl alcohol may comprise from about 0.5% to about 5% of the composition by weight, from about 1% to about 4% of the composition by weight, or from about 2% to about 3% of the composition by weight. The fatty alcohol may comprise from about 0.1% to about 5% of the composition by weight, from about 0.5% to about 4% of the composition by weight, or from about 1% to about 3% of the composition by weight.

The entire emulsifier blend (e.g., the sucragel, the alkylaryl glucoside, the alkylaryl alcohol, and the fatty alcohol) may collectively comprise from about 3% to about 20% of the composition by weight, from about 5% to about 15% of the composition by weight, or from about 8% to about 10% of the composition by weight.

D. Emollients

An emollient is a substance which makes the external layers of the skin softer and more pliable. Emollients may increase skin hydration (i.e., water content) by reducing evaporation. Typically, synthetic petrochemical components (e.g., petrolatum, petroleum jelly), silicone-derived components (e.g., methicones such as cyclomethicone), and other non eco-friendly components are included as emollients. The present compositions advantageously may include only emollients that are naturally-derived and/or naturally-processed, while exhibiting feel and other aesthetic characteristics similar to those provided by non eco-friendly emollients. The composition may include an emollient blend including a plurality of emollients which provide different polarity characteristics. For example, different polarity characteristics may be provided by inclusion of different emollients including differing chain length and/or number of chains characteristics. For example, in an embodiment, the emollients are naturally-processed, naturally derived esters of natural alcohols and natural carboxylic acids.

In an embodiment, the naturally processed, naturally derived emollient ester may be formed from alcohols and acids each having from 4 to 30 carbon atoms, from 6 to 20 carbon atoms, or from 8 to 12 carbon atoms. Such fatty acids and fatty alcohols may be sourced from coconut, palm, or other vegetable sources. For example, coconut oil fatty acids typically include a blend of fatty acids typically including from about 8 to about 20 carbon atoms, often with the heaviest concentration around 10 to 14 carbon atoms. Similarly, coconut fatty alcohols may typically include a blend of fatty alcohols typically including from about 8 to about 20 carbon atoms, often with the heaviest concentration around 10 to 14 carbon atoms. A coco-alcohol may form an ester with a desired naturally processed, naturally derived fatty acid (e.g., caprylic acid, capric acid, lauric acid, etc.). In an embodiment, the emollient blend includes a coco-caprylate, an ester of a coco-alcohol and caprylic acid.

The blend may also include another emollient ester with a longer alcohol or acid chain length. For example, another ester emollient that may be included with the coco-caprylate is decyl cocoate, an ester of decanol and coconut fatty acid. Thus, the chain lengths of the alcohol and acid of the coco-caprylate ester are 10 to 14 (for the coco) and 8 for the caprylate, while the chain lengths of the alcohol and acid of the decyl-cocoate are somewhat longer (i.e., 10 for the decanol and 10-14 for the coco). Such different chain lengths provide different polarity characteristics between the different emollients of the emollient blend. For example, decyl cocoate is a light oil with low spreadability, and medium polarity, while coco-caprylate is of similar medium polarity, with a cyclomethicone like feel, without the inclusion of any silicone component. It is fast spreading, with a pleasant dry skin feel.

The emollient blend may further include a high polarity component, such as tricaprylin, which includes more than 2 lipid chains, as do the above described esters. For example, tricaprylin includes 3 lipid chains, each with a chain length of 8 carbon atoms. Tricaprylin is a tri-ester, or triglyceride, e.g., derived from glycerol and a fatty acid. Although tricaprylin includes equal chain lengths, each with 8 carbon atoms, it will be understood that longer or shorter chain lengths may be provided (e.g., from about 4 to about 14, about 6 to about 12, or about 8 to about 10). In addition, while in caprylin, all chain lengths are equal, in other embodiments the emollient blend may include a triglyceride in which at least one of the chain lengths differs from at least one other.

Such a triglyceride provides higher polarity characteristics than the di-ester components described above. Tricaprylin in particular provides high spreadablity, high polarity, and solvating and dispersing characteristics as well. Thus, the emollient blend may include components that differ in chain length and/or number of chains to provide differing polarity characteristics to the emollients. The specific emollient blend of the coco-esters and tricaprylin has been found by the inventors to provide a silky skin feel, without consumers characterizing the feel as "greasy".

E. Stabilizers

The inventor has found that certain emulsifiers can function as stabilizers. The addition of a naturally-derived, naturally-processed stabilizer free of polyethylene glycol (PEG) surprisingly increased the high temperature stability of the composition. The specific stabilizer employed may be an ester of a fatty acid and polyglycerin. The polyglycerin may include glycerin-based components with differing degrees of polymerization (n), but well below typical "polymer" degrees of polymerization (e.g., "n" less than or equal to about 6). For example, the value of n may be 2, 3, 4, 5, or 6. In an embodiment, the value of n is 4 (i.e., polyglycerin-4). The polyglycerin may include a blend of polyglycerols of different n values (e.g., polyglycerin-2, polyglycerin-3, polyglycerin-4, polyglycerin-5). In an embodiment, some glycerin (n=1) may also be present. In another embodiment, only diglyceride and higher polyglycerols may be present within the stabilizer (although it is understood that glycerin may be added separately to the composition, e.g., as part of the sucragel emulsifier).

The fatty acid component of the polyglyceryl ester may have a carbon chain length from 4 to 30 carbon atoms, from 6 to 20 carbon atoms, or from 8 to 12 carbon atoms. In an embodiment, the stabilizer may be polyglyceryl-4 caprate. Polyglyceryl-4 caprate has specifically been found by the present inventor to surprisingly increase the high temperature stability of the composition, as the formulation without this stabilizer was separating after about a week in a hot box (elevated temperature conditions, generally 4-50 degrees Celsius). The same formulation, but with the addition of polyglyceryl-4 caprate exhibited improved high temperature stability, preventing the separation that was previously occurring.

F. Other

Compositions of the present invention can be shelf stable for at least about six months, more preferably at least about one year using naturally-derived, naturally-processed preservative systems. One suitable preservative system comprises enzyme-based oxygen scavenging antioxidant systems as described in U.S. Pat. No. 5,972,355 which is hereby incorporated by reference in its entirety. The combination of glucose, glucose oxidase and lactoperoxidase is one example of an enzyme-based oxygen scavenging antioxidant system. The combination of glucose, glucose oxidase and lactoperoxidase is available as BIOVERT from Arch Personal Care Products, South Planfield, N.J. The total of all components in a preservative system may typically be present in amounts ranging from about 0.1% to about 5% or from about 0.25% to about 1.5% by weight of the composition.

Embodiments of the present invention specifically exclude paraben preservatives, thiazolinone preservatives, and similar synthetic preservatives, including, but not limited to methyl parabens, ethyl parabens, propyl parabens, butyl parabens, methylisothiazolinone, methylchloroisothazolinone, isobutyl parabens, and DMDM hydantoin, and combinations thereof. Of course, these preservatives would be compatible with and effective in embodiments of the present invention, but would result in formulations that do not meet the rigid standards set forth by the Natural Products Association.

Although less desirable than an eco-friendly, natural preservative or preservative system, and because such small amounts are necessary to be effective, embodiments of the present invention may contain synthetic preservatives, such as phenoxyethanol. Although not a naturally-derived, naturally-processed component, the preservative (e.g., phenoxyethanol) may be the only component that is not naturally-derived and/or naturally-processed, so that 95% or more (e.g., 97% or more, 98% or more, or 99% or more) of the components in the composition are naturally-derived, naturally-processed, or both. For example, such a composition may include 1% or less phenoxyethanol. Phenoxyethanol is an approved ingredient by the Natural Products Association.

Fragrances and/or essential oils may be added in small amounts to provide an aromatically pleasing effect. Suitable eco-friendly, natural fragrances and essential oils include those generally known to one of skill in the art. Examples include, but are not limited to, citrus essential oils, floral essential oils, and combinations thereof.

IV. EXAMPLES

The cream to powder compositions of the present invention provide easier application and better coverage as compared to simple powder compositions, while providing the benefits of a composition that quickly dries to a dry, non-greasy, silk-like feel.

Multiple cream to powder compositions were prepared. One formulation (formulation A) included *zea mays* (corn starch), water, decyl cocoate, coco-caprylate, tricaprylin, cetearyl alcohol, cetyl alcohol, *ricinus communis* (castor) seed oil, polyglyceryl-4 caprate, glycerin, caprylic/capric triglyceride, *theobroma grandifloum* seed butter, fragrance, *butyrospermum parkii* (shea) butter, *aloe barbadensis* leaf juice, *cera alba* (beeswax), cetearyl glucoside, *cocos nucifera* (coconut) oil, *glycine soja* (soybean) oil, hydrogenated castor oil, sucrose laurate, tocopherol, potassium sorbate, sodium benzoate, phenoxyethanol, amyl cinnamal, citronellol, coumarin, and linalool.

The composition included about 28% by weight carrier water (not including water possibly present as portions of other components), and about 43% corn starch. The emulsifier blend included sucragel (e.g., glycerine, capric triglyceride, and the sucrose laurate), as well as cetearyl glucoside, cetearyl alcohol, and cetyl alcohol. The polyglyceryl-4 caprate also serves as an emollient, while greatly improving the high temperature stability of the composition. The emollient blend included cococaprylate, decyl cocoate, and tricaprylin. The composition had a pH from about 4.5 to about 6.0, and exhibited a thick, cream like consistency and viscosity characteristics upon dispensing from a container. Specific gravity of the composition was about 1.13 to about 1.14. Upon dispensing, the material is sufficiently thick to generally hold the shape in which it is dispensed, and dries to that general shape upon evaporation of water. The composition can be spread into or onto the skin, and rapidly disappears, so as to not leave any readily visible layer when viewed on the skin. It quickly dries to a powdery feel, similar to that of a simple powder composition when applied to the skin.

Another formulation (formulation B) included similar ingredients, but with slightly lower corn starch (e.g., about 38%) and slightly higher water concentration (about 34%). Formulation B included *zea mays* (corn starch), water, decyl cocoate, coco-caprylate, tricaprylin, cetearyl alcohol, cetyl alcohol, *ricinus communis* (castor) seed oil, polyglyceryl-4 caprate, glycerin, caprylic/capric triglyceride, *butyrospermum parkii* (shea) butter, fragrance, *theobroma grandifloum* seed butter, phenoxyethanol, beeswax, *cocos nucifera* (coconut) oil, cetearyl glucoside, sucrose laurate, hydrogenated castor oil, *aloe barbadensis* leaf juice, tocopherol, *glycine soja* (soybean) oil, potassium sorbate, and sodium benzoate. Formulation B exhibited similar characteristics as those described above relative to formulation A.

Various types of testing were performed on the compositions. The composition was tested for stability, specifically its ability to not separate over time under different conditions. The color, odor, and appearance stability characteristics were also evaluated. Samples were stored at room temperature, below room temperature (e.g., 4° C.), at elevated temperatures (e.g., 40° C. and 50° C.), and through daily freeze/thaw cycles. After 3 months, no separation or other stability issues were apparent. As described above, previous prepared formulations not including the polyglyceryl-4 caprate exhibited some tendency to phase separate after as little as a week at elevated temperature. The increased stability provided by the polyglyceryl-4 caprate was particularly advantageous, surprising, and unexpected.

Formulation A was tested for dermal irritation characteristics and exhibited no significant skin reaction. Testing was also performed by parents using the product on infant children. Significant fractions of those evaluating the formulation reported that the product kept skin dry between diaper changes, that the product felt as it if dried to a powder on the skin, that it left the skin feeling powdery soft, that the product was easy to apply (e.g., much easier than a simple powder product), that the product was less messy to use than baby powder, and that they would use the product instead of baby powder or their current diaper cream or ointment.

Another test was performed to assess the barrier properties of the formulation. Using a dye exclusion test, it was found that the barrier created by application of the formulation prevented approximately 70% of the test dye from reaching the skin, meaning that the formulation provided a significant barrier to wetness, which is particularly desirable in a composition intended for use as a baby powder.

While the present invention has been described with reference to what are presently considered to be the preferred embodiments, it is to be understood that the invention is not limited to these embodiments. To the contrary, the invention is intended to cover various modifications and equivalent arrangements included within the spirit and scope of the appended claims.

We claim:

1. A personal care composition that applies as a cream and quickly dries to a powdery feel, the composition comprising:
   (a) water, the water comprising no more than about 35% of the composition by weight;
   (b) one or more natural starch components, the natural starch components comprising at least about 35% of the composition by weight, wherein at least one of the natural starch components is corn starch;
   (c) one or more emulsifiers, wherein the one or more emulsifiers are selected from the group consisting of a sugar ester, an alkylaryl glucoside, an alkylaryl alcohol, and a fatty alcohol and combinations thereof; and
   (d) one or more emollients, wherein the one or more emollients are selected from the group consisting of coco-caprylate, decyl-cocoate, tricaprylin and combinations thereof;
   wherein (a)-(d) are naturally derived, naturally processed, or both; and
   wherein the composition does not include cyclomethicone, other methicones, or other silicone-derived components.

2. A personal care composition as recited in claim 1, wherein the composition comprises a greater fraction of natural starch components than water.

3. A personal care composition as recited in claim 2, wherein the composition comprises at least 40% natural starch components and less than 30% water.

4. A personal care composition as recited in claim 1, wherein the composition is substantially free of volatile components having a volatility greater than that of water.

5. A personal care composition as recited in claim 1, wherein the composition is substantially free of ethoxylates, acrylate copolymers, and isothiazolinones.

6. A personal care composition as recited in claim 1, further comprising a stabilizer, wherein said staiblizer comprises an ester of a fatty acid and polyglycerin.

7. A personal care composition as recited in claim 6, wherein the stabilizer comprises polyglyceryl-4 caprate.

8. A personal care composition as recited in claim 1, wherein the composition further comprises wax, the composition being thickened with wax and the one or more emulsifiers.

9. A personal care composition that applies as a cream and quickly dries to a powdery feel, the composition comprising:
   (a) water, the water comprising no more than 35% of the composition by weight;
   (b) one or more natural starch components, the natural starch components comprising at least about 35% of the composition by weight, the starch components having a greater concentration than the water in the composition, and wherein at least one of the natural starch components is corn starch;
   (c) an emulsifier and thickener blend, the emulsifier and thickener blend comprising a sugar ester and wax; and
   (d) an emollient blend, wherein the emollients in the emollient blend are selected from the group consisting of coco-caprylate, decyl-cocoate, and tricaprylin;
   (e) a stabilizer comprising polyglyceryl-4 caprate;
   wherein (a)-(e) are naturally derived, naturally processed, or both; and wherein the composition does not include cyclomethicone, other methicones, or other silicone-derived components.

10. A personal care composition as recited in claim 9, wherein the composition is substantially free of volatile components having a volatility greater than that of water.

11. A personal care composition as recited in claim 9, wherein the composition is substantially free of ethoxylates, acrylate copolymers, and isothiazolinones.

12. A personal care composition that applies as a cream and quickly dries to a powdery feel, the composition comprising:
   (a) water, the water comprising no more than 35% of the composition by weight;
   (b) one or more natural starch components, the natural starch components comprising at least about 35% of the composition by weight, the starch components having a greater concentration than the water in the composition, and wherein at least one of the natural starch components is corn starch;
   (c) an emulsifier and thickener blend, the emulsifier and thickener blend comprising a sugar ester, wax, an alkylaryl glucoside, an alkylaryl alcohol, and a straight chain fatty alcohol; and
   (d) an emollient blend, the emollient blend comprising at least two of coco-caprylate, decyl-cocoate, and tricaprylin;
   (e) one or more stabilizers, the one or more stabilizers comprising an ester of a fatty acid and polyglycerin;
   wherein (a)-(e) are naturally derived, naturally processed, or both; and
   wherein the composition does not include cyclomethicone, other methicones, or other silicone-derived components.

13. A personal care composition as recited in claim 12, wherein the composition is substantially free of volatile components having a volatility greater than that of water.

14. A personal care composition as recited in claim 12, wherein the stabilizer comprises polyglyceryl-4 caprate.

\* \* \* \* \*